United States Patent
Kimura

(10) Patent No.: US 10,406,083 B2
(45) Date of Patent: Sep. 10, 2019

(54) COSMETIC

(71) Applicant: JO Cosmetics Co., Ltd., Tokyo (JP)

(72) Inventor: Hiroko Kimura, Tokyo (JP)

(73) Assignee: JO Cosmetics Co., Ltd., Ota-ku, Tokyo (JP)

( * ) Notice: Subject to any disclaimer, the term of this patent is extended or adjusted under 35 U.S.C. 154(b) by 26 days.

(21) Appl. No.: 15/548,567

(22) PCT Filed: Jan. 28, 2016

(86) PCT No.: PCT/JP2016/052418
§ 371 (c)(1),
(2) Date: Aug. 3, 2017

(87) PCT Pub. No.: WO2016/132841
PCT Pub. Date: Aug. 25, 2016

(65) Prior Publication Data
US 2018/0000702 A1  Jan. 4, 2018

(30) Foreign Application Priority Data

Feb. 17, 2015 (JP) ................ 2015-028113

(51) Int. Cl.
*A61K 8/25* (2006.01)
*A61Q 1/12* (2006.01)
*A61K 8/02* (2006.01)
*A61Q 17/04* (2006.01)
*A61K 8/06* (2006.01)
*A61Q 1/02* (2006.01)

(52) U.S. Cl.
CPC .............. *A61K 8/25* (2013.01); *A61K 8/0266* (2013.01); *A61K 8/062* (2013.01); *A61Q 1/02* (2013.01); *A61Q 1/12* (2013.01); *A61Q 17/04* (2013.01); *A61K 2800/262* (2013.01); *A61K 2800/412* (2013.01)

(58) Field of Classification Search
CPC ................ A61K 8/25; A61K 8/0266
See application file for complete search history.

(56) References Cited

U.S. PATENT DOCUMENTS

| | | | |
|---|---|---|---|
| 4,830,843 A | 5/1989 | Usui et al. | |
| 2013/0343980 A1* | 12/2013 | Le Roux | C01B 33/22 423/331 |

FOREIGN PATENT DOCUMENTS

| | | |
|---|---|---|
| JP | 61-10020 A | 1/1986 |
| JP | 61-141587 A | 6/1986 |
| JP | 03-51651 B2 | 8/1991 |
| JP | 2007-045800 A | 2/2007 |
| JP | 2008-088041 A | 4/2008 |
| JP | 2009-179540 A | 8/2009 |
| JP | 2009-543754 A | 12/2009 |
| JP | 2014-520743 A | 8/2014 |
| WO | WO-2012085239 A1 * | 6/2012 ............. C01B 33/22 |

OTHER PUBLICATIONS

"Talc as used in cosmetics" Scientific Literature Review, Aug. 15, 2012, pp. 1-3 and 28.*
Angela Dumas et al., "Phyllosilicates synthesis: a way of accessing edges contributions in NMR and FTIR spectroscopies. Example of synthetic talc", Phys Chem Minerals, 2013, pp. 361-373, 40.
International Search Report for PCT/JP2016/052418, dated Apr. 26, 2016.

* cited by examiner

*Primary Examiner* — Gina C Justice
(74) *Attorney, Agent, or Firm* — Sughrue Mion, PLLC

(57) ABSTRACT

A cosmetic having excellent properties in transparency, spreadability, smoothness, skin compatibility and safety is prepared using a synthetic talc that is flake-like particles containing 2:1-type laminar crystals of silicate which have a basic structure of an octahedron sheet sandwiched between two tetrahedron sheets. The flake-like particle has a mean volume particle diameter of 0.5 to 100 μm, and 0.3° or less of half width at half maximum of peak present at $2\theta$ equal to $9.4° \pm 1°$ when measured by unoriented powder X-ray diffractometry (XRD) using CuKα rays, and the cosmetic is substantially free of $Mg_3Si_2O_5(OH)_4$.

15 Claims, No Drawings

COSMETIC

CROSS REFERENCE TO RELATED APPLICATIONS

This application is a National Stage of International Application No. PCT/JP2016/052418 filed Jan. 28, 2016, claiming priority based on Japanese Patent Application No. 2015-028113 filed Feb. 17, 2015, the contents of all of which are incorporated herein by reference in their entirety.

DETAILED DESCRIPTION OF THE INVENTION

Technological Field

The present invention relates to a cosmetic which contains a synthetic talc and is excellent in feel during use and safety.

Background Technology

Conventionally, various kinds of powders have been used in production of cosmetics according to their intended use or application. Such a powder has been appropriately selected from natural powders, synthetic powders or composite powders thereof, taking into account organoleptic characteristics and feel during use such as smoothness. Of these, talc has been used for many years to improve transparency, spreadability and smoothness of cosmetics because it is a slippery material having a flat and sheet shaped crystal as represented by the name "kasseki" which means a slippery stone in Japanese, and is a very soft mineral having 1 Mohs hardness as well as a good transparent appearance. However, since talc used for cosmetics is a fine powder prepared by pulverizing a natural mineral, there is a problem that preparation of the fine particle needs time-consuming operations of pulverization and classification. In the case that the fine powder is prepared by pulverizing natural talc, surface smoothness and flat shape are apt to be impaired as pulverization of the talc proceeds, and a ratio of long diameter in crystal plane (a, b) to a length in c-axis direction (thickness), i.e. thickness aspect ratio becomes smaller. Use of such talc powders deteriorated in surface smoothness and flatness as an extender pigment for cosmetics causes a problem that transparency and smoothness of cosmetics are impaired.

In order to solve such problems, for example, Patent document 1 proposes a production method for producing a silicate mineral powder wherein a silicate mineral such as talc is pulverized and classified, and subsequently a powder having a mean diameter of less than 5 μm is removed in the step of elutriation which is an additional step. The document discloses that incorporation of talc powders obtained by the production method into cosmetics brings in improvement of smoothness and reduction of roughness when applied to skin surface (see paragraph 0039).

Patent document 2 proposes a production method for producing a fine talc powder having a median diameter $D_{50}$ of 0.1 to 2 μm measured by a laser diffraction and scattering method wherein talc particles having a median diameter $D_{50}$ over 2 μm are accelerated using a jet stream to collide each other or with a collision board (see claim 5). The document also discloses that the production method is effective for preventing aggregation of fine talc powders (see paragraph 0009). However, as long as fine particles are prepared by mechanically pulverizing talc particles, causing broadening of particle size distribution, deterioration of surface smoothness and decrease of an aspect ratio cannot be avoided.

Hence, cosmetics containing particles prepared by pulverizing natural talc are insufficient in feel during use such as skin compatibility or smoothness and fineness upon finishing, and transparency. Therefore, improvement of such drawbacks has been demanded.

Further, purity of natural talc and properties of impurities contained in the natural talc depend on a mineral deposit. Depending on the species of natural talc to be used, there is a risk that natural talc may contain asbestos such as chrysotile (serpentine, chemical constitution: $Mg_3Si_2O_5(OH)_4$) which is a banned substance. Therefore, use of natural talc has a problem that special consideration to ensure safety is required.

Conventionally, use of synthetic talc powder in place of natural-derived talc has been proposed. For example, Patent document 3 discloses that synthetic layered phyllosilicate having a three-layered structure in which an octahedron sheet of $MgO_6$ is sandwiched between two tetrahedron sheets of $SiO_4$, and a BET specific surface area of 300 m$^2$/g or more is obtained by hydrothermal synthesis from active silica or active aluminosilicate and magnesium hydroxide, and the synthetic layered phyllosilicate can be used as a material for cosmetics such as various kinds of milky lotions, creams and lotions. In examples 1 to 4 of the document, it is disclosed that hydrothermal synthesis reaction of a slurry containing $SiO_2$ and magnesium hydroxide is conducted at 160° C., and then the resultant reaction products is cooled, dried and pulverized using a mill to use as a sample, and the synthetic layered phyllosilicates obtained in the examples have a large stacking disorder index, a large BET specific surface area and a large methylene blue decoloring power, and are superior in emulsifying property as compared with magnesium silicate having a low crystallinity used in the comparative examples. The method disclosed in the examples of the document however needs a pulverization step for preparing fine particles, which is a time-consuming step, as with the case of natural talc. Besides, it is difficult to control particle size distribution since a large amount of very fine particles are contained as seen from the fact that BET specific surface area is very large.

Patent document 4 discloses a method for producing mineral particles composed of silicon and metal, and having a form very similar to natural talc by hydrothermal treatment of silicon and metal gel which is conducted at 300° C. to 600° C. (see claim 1). The document also discloses that natural talc is used in many industrial fields such as cosmetics (see paragraph 0003). However, as the document has no sufficient disclosure concerning a form of synthetic talc obtained, it is indefinite what kind of synthetic talc is obtained. X-ray diffraction spectrum of synthetic talc prepared by the method is shown in FIG. 4. The peak in direction of c axis (001) shown in the spectrum is definitely broader as compared with that of natural talc. This fact means that the synthetic talc has a lower crystallinity as compared with natural talc. Besides, the document neither discloses any example relative to cosmetics containing the synthetic talc, nor provides any information concerning what kind of physical properties and characteristic are necessary for a synthetic talc to be used in a cosmetic field.

In relation to the method described in Patent document 4, Patent document 5 discloses a method for preparing a hydrogel precursor of metallic mineral particles in the presence of carboxylic acid (see claim 1). The document discloses that, according to the method, a hydrothermal reaction can be carried out at a temperature of 150° C. to 400° C. (see claim 12). However, the document does not provide sufficient disclosure about the shape of synthetic talc obtained, and does not reveal what kind of synthetic talc is obtained.

On the other hand, Non-patent document 1 authored by the inventors of Patent document 5 discloses various kinds of physical property values, such as shape of particles, BET specific surface area and thermogravity analytical data relative to various kinds of synthetic talcs obtained in experiments wherein production conditions are varied from those in Patent document 5. The document reports the following based on analysis of the experimental results.

(1) Both length in the c* direction and length in the (ab) plane linearly increase with increase of the hydrothermal treatment duration. Crystal size coherency (CSC) in the c* direction and in the (ab) plane at a hydrothermal treatment duration of one hour are respectively 230 Å and 100 Å whereas CSC at a hydrothermal treatment duration of over 1,000 hours are respectively increased to 410 Å and 400 Å (see page 363, right column and page 364, FIG. 3).

(2) Synthetic talc at a hydrothermal treatment duration of 60 days has a half CSC in the c* direction as compared with natural talc, and contains a stack of micron-sized particles and finer particles of around 200 nm (see page 363, right column, page 364, right column and page 366, FIG. 5).

(3) The more the hydrothermal treatment duration increases, the more BET specific surface area of synthetic talc decreases. BET specific surface area of synthetic talc is 28 m²/g at a hydrothermal treatment duration of 60 days which is still larger than that of natural talc since BET specific surface area of natural talc is 20 m²/g at most (page 364, right column and page 367, FIG. 6).

As indicated in Non-patent document 1, synthetic talc having a far larger BET specific surface area as compared with natural talc is merely obtained in the production methods disclosed in Patent documents 4 and 5. Even in the case that hydrothermal treatment duration is 60 days when BET specific surface area becomes minimum, the synthetic talc had a BET specific surface area of 28 m²/g that is over 20 m²/g being a maximum value of natural talc, and still contained very fine particles. In addition, the document discloses nothing about use of the synthetic talc as a material for cosmetics.

PRIOR ART DOCUMENT

Patent Document

Patent Document 1: Japanese Unexamined Patent Application Publication No. 2009-179540
Patent Document 2: Japanese Unexamined Patent Application Publication No. 2008-088041
Patent Document 3: Japanese Patent Publication No. 1991-51651
Patent Document 4: Japanese Unexamined Patent Application Publication No. 2009-543754
Patent Document 5: Japanese Unexamined Patent Application Publication No. 2014-520743

Non-Patent Document

Non-Patent Document 1: Phys Chem Minerals (2013) 40: pp. 361-373

DISCLOSURE OF THE INVENTION

Problems to be Solved by the Invention

Under the aforementioned background, the present invention aims to provide a cosmetic which is excellent in transparency, feel during use such as spreadability, smoothness and fineness upon finishing, and safety.

Means Used to Solve the Problem

The present inventor has diligently studied to solve the aforementioned problems and has found that the problems can be solved by using synthetic talc, which has an enhanced crystallinity, a specified particle diameter and a specified composition, as an extender pigment or a component for a cosmetic. The present invention was completed based on the above knowledge.

Thus, the present invention provides the following cosmetics.

(1) A cosmetic comprising a synthetic talc, wherein the synthetic talc is a flake-like particle that has a basic structure in which an octahedron sheet is sandwiched between two tetrahedron sheets and contains a 2:1 type layered crystal silicate represented by formula (1);

$$Mg_xSi_yO_{10}(OH)_2 \qquad (1)$$

in the formula (1), x and y are values satisfying conditions of $0.50 \leq x/y \leq 1.20$ and $6.5 \leq x+y \leq 7.5$, wherein the flake-like particle has a mean volume particle diameter of 0.5 to 100 μm and 0.3° or less of half width at half maximum of peak existing at 2θ equal to 9.4°±1° when measured by unoriented powder X-ray diffractometry (XRD) using CuKα ray, and is substantially free of $Mg_3Si_2O_5(OH)_4$.

(2) The cosmetic according to (1), wherein the flake-like particle has a variation coefficient of particle size distribution of 30% or less.

(3) The cosmetic according to (1) or (2), wherein the flake-like particle has a BET specific surface area of 2 to 25 m²/g.

(4) The cosmetic according to any one of (1) to (3), wherein peak existing at 2θ equal to 9.4°±1° when measured by unoriented powder X-ray diffractometry (XRD) is twice or more in its intensity as compared to peak existing at 2θ equal to 60.5°±1°.

(5) The cosmetic according to any one of (1) to (4), wherein the flake-like particle has 0.3 to 0.8 of a ratio of a mean short diameter to a mean long diameter in its crystal plane (a, b) (mean short diameter/mean long diameter), 0.01 to 1 μm of a mean thickness relative to its c-axis direction, and 10 to 500 of a mean aspect ratio (mean long diameter/mean thickness).

(6) The cosmetic according to any one of (1) to (5), wherein the flake-like particle has 0.40 or less of a mean friction coefficient (MIU) and 0.0035 or less of a fluctuation of mean friction coefficient (MMD).

(7) The cosmetic according to any one of (1) to (6), wherein the flake-like particle is a non-pulverized particle which is obtained by hydrothermal synthesis.

(8) The cosmetic according to any one of (1) to (7), wherein the flake-like particle is obtained by a process comprising a step for preparing a raw material containing a magnesium hydroxide powder and a silica powder, and a step for conducting hydrothermal synthesis by heating the raw material at a temperature of 500° C. to 800° C. under a pressure of 100 to 5,000 bar.

(9) The cosmetic according to any one of (1) to (8), wherein the cosmetic is a powder cosmetic.

(10) The cosmetic according to any one of (1) to (8), wherein the cosmetic is in the form of a liquid, milky lotion or cream.

Effects of the Invention

The cosmetic of the present invention is excellent in transparency, spreadability, skin compatibility and fineness upon finishing as compared with conventional natural talcs. Also, the cosmetic of the present invention is excellent in safety since the synthetic talc used for the cosmetic does not contain a toxic substance such as chrysotile.

(Synthetic Talc)

The synthetic talc used in the present invention is a flake-like particle that has a basic structure in which an octahedron sheet is sandwiched between two tetrahedron sheets and contains a 2:1 type layered crystal silicate represented by following formula (1);

$$Mg_xSi_yO_{10}(OH)_2 \quad (1)$$

in the formula (1), x and y are values satisfying conditions of $0.50 \leq x/y \leq 1.20$ and $6.5 \leq x+y \leq 7.5$.

The synthetic talc has a mean volume particle diameter of 0.5 to 100 μm and 0.3° or less of half width at half maximum of peak existing at 2θ equal to $9.4°\pm1°$ when measured by unoriented powder X-ray diffractometry (XRD) using CuKα ray, and is substantially free of $Mg_3Si_2O_5(OH)_4$.

When a ratio of Mg and Si in the synthetic talc (i.e. x/y) is outside the defined range, it becomes difficult to obtain a flat particle having a smooth surface. Cosmetics containing particles obtained under conditions being outside the defined range of x/y ratio tend to deteriorate transparency, spreadability, smoothness and skin compatibility. In this view, the ratio of Mg to Si is preferably $0.70 \leq x/y \leq 1.15$, more preferably $0.80 \leq x/y \leq 1.10$. For reference, the chemical stoichiometry of Mg/Si (x/y) in magnesium silicate is 0.75.

When a cosmetic contains particles having a mean volume particle diameter of less than 0.5 μm, the cosmetic tends to deteriorate transparency, spreadability and smoothness. By contrast, when a cosmetic contains particles having a mean volume particle diameter of more than 100 μm, the cosmetic tends to deteriorate roughness when applied to skin, and to deteriorate skin compatibility. The mean volume particle diameter is preferably 1 to 50 μm, more preferably 1 to 30 μm. The mean volume particle diameter can be measured using a laser diffraction particle size distribution analyzer (e.g. LA-950 by Horiba Ltd.).

In powder X-ray diffractometry (XRD) using CuKα ray, a half width at half maximum of peak existing at 2θ equal to $9.4°\pm1°$ has been known as an index to indicate a degree of crystallization of c axial direction. When the value exceeds 0.3°, resultant particles do not become a flat crystal with a smooth surface, and a cosmetic containing such a synthetic talc becomes insufficient in transparency, spreadability, smoothness and skin compatibility. Although a value of the half width at half maximum is preferred to be as small as possible, difficulty on production of particles increases with decrease of the value. From such a viewpoint, the half width at half maximum is preferably 0.03° to 0.3°, more preferably 0.05° to 0.2°, most preferably 0.07° to 0.15°.

The synthetic talc used in the present invention is substantially free of chrysotile. The term "substantially free" means that, when measured according to X-ray diffraction method described in Labor Standards Bureau Notification No. 0828001 by Ministry of Health, Labor and Welfare, content of $Mg_3Si_2O_5(OH)_4$ is equal to the detection limit (0.1% by mass) or less.

The synthetic talc preferably has a variation coefficient of particle size distribution of 30% or less, more preferably 25% or less in measurement using a laser diffraction/dispersion particle size distribution analyzer. When the variation coefficient of particle size distribution is excessively large, contents of a very fine particle and a coarse particle increase. Consequently, a cosmetic containing such a synthetic talc tends to become insufficient in transparency, spreadability and fineness upon finishing. The variation coefficient of particle size distribution is calculated by the following formula.

Variation coefficient CV (%)=100×(standard deviation of particle size distribution/mean volume particle size)

The synthetic talc preferably has a BET specific surface area of 2 to 25 m²/g, in particular, 3 to 20 m²/g. Synthetic talc having a BET specific surface area over 25 m²/g contains an increased amount of very fine particles, thereby a cosmetic containing such a synthetic talc tends to be impaired in transparency, spreadability and smoothness. While, a cosmetic containing a synthetic talc having a BET specific surface area less than 2 m²/g tends to deteriorate in roughness when applied to skin, and to be impaired in skin compatibility. BET specific surface area can be measured by the BET method.

The synthetic talc has preferably a mean long diameter in its crystal plane (a, b) of 0.1 to 100 μm, in particular, 0.5 to 30 μm, a ratio of a mean short diameter to a mean long diameter (short diameter/long diameter) of 0.3 to 0.8, a mean thickness in its c-axis direction of 0.01 to 1 μm, in particular, 0.02 to 0.3 μm, and a mean aspect ratio (mean long diameter in the plane/mean thickness) of 10 to 500, preferably 15 to 300, in particular, 20 to 100. A cosmetic containing, as an extender pigment, a synthetic talc which has an excessively small mean aspect ratio, an excessively short mean long diameter in its crystal plane or an excessively large mean thickness tends to become insufficient in transparency, spreadability, smoothness and skin compatibility. While, a cosmetic containing a synthetic talc which has an excessively large mean aspect ratio, an excessively long mean long diameter in its crystal plane or an excessively small mean thickness tends to cause fracture of particles during its production step, thereby quality of the cosmetic tends to become unstable.

The synthetic talc to be used is preferred to have twice or more, in particular, 2.5 times or more of intensity relative to peak existing at 2θ equal to $9.4°\pm1°$ (2θ=$9.4°\pm1°$) as compared to that relative to peak existing at 2θ equal to $60.5°\pm1°$ when measured by unoriented powder X-ray diffractometry (XRD). When the ratio is less than 2, resultant particles do not tend to become a flat crystal with a smooth surface, and a cosmetic containing such a synthetic talc tends to become insufficient in transparency, spreadability, smoothness and skin compatibility.

The synthetic talc to be used in the present invention preferably has a mean friction coefficient (MIU) of 0.40 or less and a fluctuation of the mean friction coefficient (MMD) of 0.0035 or less, more preferably a mean friction coefficient (MIU) of 0.30 or less and a fluctuation of the mean friction coefficient (MMD) of 0.0030 or less. As MIU becomes smaller, a cosmetic containing such a synthetic talc becomes excellent in spreadability and slidability. As MMD becomes smaller, a cosmetic containing such a synthetic talc tends to be improved in roughness and smooth feeling. Mean friction coefficient (MIU) and its fluctuation (MMD) can be measured using a friction tester (KES-SE available from Kato Tech Co., Ltd).

The synthetic talc to be used in the present invention preferably has a 2% by mass-reduction temperature of 800° C. to 900° C. and a 5% by mass-reduction temperature of 900° C. to 1,000° C. in thermogravity analysis (TG). When the mass-reduction temperature is below the range, synthetic talc sometimes does not become a flat crystal having smooth surface. A cosmetic containing such a synthetic talc tends to become insufficient in transparency, spreadability, smoothness and skin compatibility.

If needed, the above-mentioned synthetic talc may be treated with an agent for making its surface hydrophorbic such as silicone, metal soap, fatty acid, acylated fatty acid, fluorine compound, oil and surfactant, or may be treated with acid, alkali or inorganic salt. Also, the synthetic talc may be treated in combination of these methods. Of these, synthetic talc having a hydrophobized surface is preferred in view of providing a cosmetic which is excellent in feel during use and water resistance.

(Production Process of Synthetic Talc)

The above-mentioned synthetic talc can be obtained by a hydrothermal synthesis method, wherein raw materials containing magnesium and silicon respectively is prepared, and then a mixture of the raw materials is heated at a high temperature under a high pressure. Examples of the raw material containing magnesium include magnesium hydroxide, magnesium oxide, alkoxide of magnesium and Brucite which is a mineral containing magnesium. Of these, magnesium hydroxide and Brucite are preferred. Examples of the raw material containing silicon include silica and sodium silicate. Of these, silica is preferred. Each of raw materials containing respectively magnesium and silicon is preferably prepared as a powder, and then mixed. Subsequently, thus-obtained powdered mixture is supplied to a hydrothermal synthesis apparatus. Such a procedure is preferred in view of operability and economic efficiency. In particular, use of powdered magnesium hydroxide and powdered silica is preferred.

Condition of pressurization in the hydrothermal synthesis is usually 100 to 5,000 bar, preferably 200 to 3,000 bar, and reaction temperature is usually 500° C. to 800° C., preferably 550° C. to 700° C. Production of impurities can be suppressed by maintaining the reaction temperature to be equal to or below the above-mentioned upper limit. As a hydrothermal synthesis apparatus, there can be used a test tube type reaction vessel, Morey type reaction vessel, autoclave and the like. Reaction time is usually from 1 hour to ten days. When the pressure and the temperature are excessively low or the reaction time is excessively short, it is difficult to obtain a synthetic talc having predetermined crystal structure, particle diameter and particle shape because crystallization does not proceed sufficiently. Therefore, it is preferable to choose these conditions appropriately. The hydrothermal synthesis is preferably carried out without internal agitation of a reaction vessel to proceed with crystallization efficiently.

Such hydrothermal synthesis method makes it possible to synthesize particles having a narrow particle size distribution, and further to synthesize particles with a small size without carrying out the milling operation which is considered indispensable for natural talc. The greatest benefit of the hydrothermal synthesis is that a powder-like synthetic talc is obtained upon completion of the reaction. Therefore, it is possible to break down aggregates contained in the powder-like synthetic talc by merely conducting a simple cracking operation. Since this method makes it possible to synthesize predetermined synthetic talcs without carrying out the milling operation, production of very fine particles due to the milling operation observed in the conventional methods does not occur. Hence, it is possible to synthesize a flake-like particle having a small BET specific surface area and a small variation coefficient of particle size distribution, and being excellent in flatness of surface, slidability and smoothness.

(Cosmetic)

The cosmetic of the present invention contains the above-mentioned flake-like synthetic talc as an extender pigment or a main component of the cosmetic. Content of the flake-like synthetic talc in the cosmetic is not necessarily constant, and depends on the kind of cosmetics. When the cosmetic is a powdered cosmetic, the content is preferably 1 to 99% by mass, more preferably 5 to 80% by mass relative to the entire amount. When the cosmetic is a milky lotion cosmetic such as emulsified foundation, milky-lotion makeup base and milky-lotion for sunscreen, the content is preferably 0.1 to 30% by mass, more preferably 0.5 to 20% by mass relative to the entire amount. In the case that the cosmetic contains the flake-like synthetic talc as a extender in the above-mentioned range, it becomes possible to obtain efficiently a cosmetic which is excellent in transparency, spreadability on skin, smoothness, skin compatibility. Further, in the case of a product such as baby powder, the product can be prepared by using the synthetic talc solely without other component for a cosmetic.

The cosmetic of the present invention is suitable for skin care cosmetic, makeup cosmetic, hair cosmetic, antiperspirant, baby powder and the like. In particular, it is suitable for a makeup cosmetic such as face powder, solid face powder, eye shadow, rouge, makeup base, nail enamel, eyeliner, mascara, lipstick and the like.

The cosmetic of the present invention may contain components other than the synthetic talc which is allowed to used in the cosmetic field, for example, other flake-like particles, various kind of color pigments, extender pigment, aqueous component, oily component and the like.

The above-mentioned color pigment is not limited. Examples of the color pigment include inorganic white pigment such as titanium dioxide and zinc oxide; inorganic red pigment such as iron oxide (red ocher) and iron titanate; inorganic brown pigment such as γ-iron oxide; inorganic yellow pigment such as yellow oxide of iron and ocher; inorganic black pigment such as black oxide of iron and low order titanium oxide; inorganic purple pigment such as manganese violet and cobalt violet; inorganic green pigment such as chromium oxide, chromium hydroxide and cobalt titanate; inorganic blue pigment such as ultramarine and prussian blue; pearl pigment such as mica coated with titanium oxide, bismuth oxychloride coated with titanium oxide, talc coated with titanium oxide, mica coated with coloring titanium oxide, bismuth oxychloride and fish scales; metallic powder pigment such as aluminum powder, copper powder; organic colors such as red No. 201, red No. 202, red No. 204, red No. 205, red No. 226, yellow No. 401 and blue No. 404; and natural color such as chlorophyll and β-carotene.

The above-mentioned extender pigment is not limited. Examples of the extender pigment include mica, synthetic mica, sericite, talc other than the above-mentioned synthetic talc, kaolin, calcium carbonate, magnesium carbonate, barium sulfate and aluminum oxide.

Both the aqueous component and the oily component are not limited. They may contain a component such as oil, surfactant, moisturizer, higher alcohol, sequestering agent, natural or synthetic polymer, water soluble or oil soluble polymer, ultraviolet ray absorbent, various extraction liquids, antiseptic, antioxidant, pigment, dye, thickener, pH adjuster, fragrance, cool feeling agent, antiperspirant, disinfectant, and skin activator. Specifically, it is possible to make a desired cosmetic by appropriately adding components listed below solely or in combination of two or more components in accordance with the usual method. Content of additional components is not limited as long as it is in a range where the effect of the present invention is not substantially impaired.

The oil is not limited. Examples of the oil include avocado oil, camellia oil, turtle oil, macadamia nuts oil, corn oil, mink oil, olive oil, rapeseed oil, egg yolk oil, sesame oil, apricot kernel oil, wheat germ oil, *Camellia sinensis* leaf oil, castor oil, flaxseed oil, safflower oil, cottonseed oil, perilla oil, soybean oil, jojoba oil, glyceryl trioctanoate, glyceryl tri-isopalmitate, cacao fat, coconut oil, horse fat, hydrogenated coconut oil, palm oil, beef tallow, mutton tallow, hydrogenated beef tallow, palm kernel oil, hydrogenated castor oil, bees wax, candelilla wax, carnauba wax, liquid paraffin, ozocerite, paraffin, ceresin, squalane, petrolatum, microcrystalline wax, polyethylene wax, synthetic wax, silicone oil and the like.

The lipophilic non-ionic surfactant is not limited. Examples of the lipophilic non-ionic surfactant include esters of sorbitan and fatty acid such as sorbitan monooleate, sorbitan monoisostearate, sorbitan monolaurate, sorbitan monopalmitate, sorbitan monostearate, sorbitan sesquioleate, sorbitan trioleate, penta-2-ethylhexyl acid diglycerol sorbitan ester and tetra-2-ethylhexyl acid diglycerol sorbitan ester; glycerin/polyglycerin fatty acid esters such as monoester of glycerin and cottonseed oil fatty acid, monoester of glycerin and erucic acid, glyceryl sesquioleate, glyceryl mono-stearate, glyceryl α,α'-oleate/pyroglutamate and glyceryl mono-stearate/malate; esters of propylene glycol and fatty acid such as propylene glycol mono-stearate; hydrogenated castor oil derivatives, glycerin alkyl ether and the like.

The hydrophilic non-ionic surfactant is not limited. Examples of the hydrophilic non-ionic surfactant include esters of POE-sorbitan and fatty acid such as POE-sorbitan monooleate and POE-sorbitan monostearate; esters of sorbitol and fatty acid such as POE-sorbitol mono-laurate and POE-sorbitol monooleate; esters of glycerin and fatty acid such as POE-glyceryl mono-stearate and POE-glyceryl mono-isostearate; esters of POE and fatty acid such as POE mono-oleate, POE di-stearate; POE alkyl ethers such as POE lauryl ether and POE oleyl ether; POE/POP alkyl ethers such as POE/POP cetyl ether, POE/POP 2-decyltetradecyl ether and POE/POP monobutyl ether; condensations of tetra POE/tetra POP and ethylenediamine such as Tetronic®; POE hydrogenated castor oil derivatives such as POE hydrogenated castor oil, POE hydrogenated isostearate and POE hydrogenated tri-isostearate; alkanolamide such as coconut oil fatty acid diethanolamide, lauric acid monoethanolamide and fatty acid isopropanol amide; POE propylene glycol fatty acid ester, POE alkylamine, POE fatty acid amide, sucrose fatty acid ester and the like.

Surfactants other than the above-mentioned surfactants may be added as long as addition of such surfactants does not cause any problem in stability and skin irritation. Examples of the surfactants involve anionic surfactants such as fatty acid soap, higher alkyl sulfate, triethanolamine POE lauryl sulfate and alkyl ether sulfate; canionic surfactants such as alkyltrimethylammonium salt, alkylpyridinium salt, alkyl quaternary ammonium salt, alkyldimethylbenzylammonium salt, POE alkylamine, alkylamine salt and polyamine fatty acid derivative; and ampholytic surfactants such as imidazoline based surfactant, betaine based surfactant.

The above-mentioned moisturizer is not limited. Examples of the moisturizer include xylitol, sorbitol, maltitol, chondroitin sulfate, hyaluronic acid, collagen, sodium lactate, dl-pyrrolidone carboxylate, *Rosa roxburghii* extract, *Achillea millefolium* extract and melilot extract.

The sequestering agent is not limited, and may be 1-hydroxy ethane 1,1-diphosphonic acid, 1-hydroxyethane-1, tetrasodium 1-diphosphate, sodium citrate, sodium polyphosphate, sodium metaphosphate, gluconic acid, phosphoric acid, citric acid, ascorbic acid, succinic acid, edetic acid and the like.

The above-mentioned natural water-soluble polymer is not limited, and examples of the polymer include plant-derived polymers such as gum arabic, tragacanth gum, galactan, guar gum, carob gum, karaya gum, carrageenan, pectin, agar, quince seed (quince), algae colloid (brown algae extract), starch (rice, corn, potato, wheat) and glycyrrhizic acid; microorganism-derived polymers such as xanthan gum, dextran, succinoglycan and pullulan; animal-derived polymers such as collagen, casein, albumin and gelatin.

The semi-synthetic water-soluble polymer is not limited, and examples thereof include starch-derived polymers such as carboxymethyl starch and methyl hydroxypropyl starch; cellulose-derived polymers such as methyl cellulose, nitro cellulose, ethyl cellulose, methyl hydroxypropyl cellulose, hydroxyethyl cellulose, sodium cellulose sulfate, hydroxypropyl cellulose and sodium carboxymethylcellulose (CMC); alginic acid based polymers such as sodium alginate and propylene glycol alginate.

The synthetic water-soluble polymer is not limited, and examples thereof include vinyl monomer based polymers such as polyvinyl alcohol, polyvinyl methyl ether and polyvinyl pyrrolidone; polyoxyethylene based polymers such as polyoxyethylene glycol 20,000, 40,000, 60,000; polyoxyethylene-polyoxypropylene copolymer based polymers; acrylic polymers such as sodium polyacrylate, polyethylacrylate and polyacrylamide; polyethyleneimine and cation polymer.

The inorganic thickener is not limited, and examples thereof bentonite, aluminum magnesium silicate (veegum), laponite, hectorite and anhydrous silicic acid.

The ultraviolet ray absorbent is not limited, and examples thereof include ultraviolet ray absorbents of cinnamic acid type such as benzyl p-methoxycinnamate, 2-ethylhexyl p-methoxycinnamate and glyceryl mono-2-ethylhexanoate di-p-methoxycinnamate; ultraviolet absorbers of benzophenone type such as hydroxy methoxybenzophenone, dihydroxy methoxybenzophenone, dihydroxybenzophenone, tetra-hydroxybenzophenone; ultraviolet absorbers of benzoic acid ester type such as p-aminobenzoic acid, ethyl p-aminobenzoate, glyceryl p-aminobenzoate, amyl p-dimethylaminobenzoate, octyl p-dimethyl aminobenzoate, ethyl 4-[N,N-di-(2-hydroxypropyl)amino]benzoate and diethylamino hydroxybenzoyl hexyl benzoate; ultraviolet absorbers of salicylic acid type such as ethylene glycol salicylate, phenyl salicylate, octyl salicylate, benzyl salicylate, homomenthyl salicylate; ultraviolet absorbers of triazine type such as ethylhexyl triazone (2,4,6-tris [4-(2-ethyl hexyloxycarbonyl) anilino] 1,3,5-triazine) and bis-ethylhexyloxyphenol methoxyphenyl triazine; other ultraviolet absorbers such as 4-tert-butyl 4'-methoxy dibenzoylmethane, 5-methyl-2-isopropylcyclohexyl anthranilate, 2-(2-hydroxy-5-methylphenyl) benzotriazole, 2-ethylhexyl dimethoxybenzylidene dioxoimidazolidine propionate, octocrylene and dimethicodiethylbenzalmalonate.

The extraction liquid is not limited, and examples thereof include houttuynia extract, cork tree bark extract, melilot extrac, *Lamium album* extract, *glycyrrhiza* extract, peony extract, *Saponaria officinalis* leaf extract, *luffa cylindrica* extract, kina ekisu, saxifrage extract, *sophora* root extract, *Nuphar japonicum* extract, fennel extract, primrose extract, rose extract, *rehmannia glutisona* root extract, lemon extract, *lithospermum* root extract, aloe extract, *acorus calamus rhizome* extract, *eucalyptus* extract, *equisetium arvense* extract, sage extract, thyme extract, tea extract, seaweed extract, cucumber extract, *Eugenia Caryophyllus* flower extract, raspberry extract, *Melissa officinalis* leaf extract, carrot extract, horse chestnut extract, peach extract, peach leaf extract, mulberry extract, *centaurea cyanus* extract, *hamamelis* extract, placental extract, thymus extract, silk extract, and the like.

As other components, there can be added vitamins such as vitamin A oil, retinol, retinyl palmitate, inositol, pyridoxine hydrochloride, benzyl nicotinate, nicotinamide, DL-α-tocopheryl nicotinate, magnesium ascorbyl phosphate, 2-O-α-D-glucopyranosyl L-ascorbic acid, vitamin D2 (ergocalciferol), DL-α-tocopherol, DL-α-tocopheryl acetate, pantothenic acid and biotin; hormones such as estradiol and ethynyl estradiol; amino acids such as arginine, aspartic acid, cystine, cystein, methionine, serine, leucine and tryptophan; anti-inflammatory agents such as allantoin and azulene; skin whitening agents such as arbutin; astringents such as zinc oxide and tannic acid; fatty acid compounds such as a fatty acid, e.g. lauric acid, myristic acid, palmitic acid, stearic acid, oleic acid, isostearic acid, and a salt of the fatty acid, e.g. sodium salt, potassium salt, calcium salt, magnesium salt, strontium salt, barium salt; and cooling agents such as L-menthol and camphor.

(Production Method of Cosmetic)

The cosmetic of the present invention may be in any form such as powder, cake, pencil, stick, ointment, liquid, milky lotion and cream. Of these, powdered cosmetics such as powdered form and cake form are preferable since they exhibit remarkably improved properties in transparency, spreadability, smoothness and skin compatibility that are derived from use of the synthetic talc. Such powdered cosmetics can be prepared by mixing the synthetic talc with other powdered component in accordance with the usual method, and then adding an oil component and other component if needed, and filling the resultant mixture into a vessel or filling and compressing the resultant mixture into an aluminum pan.

Hereafter, the invention will be further explained with reference to specific examples. However, the invention is not limited by these examples. Part and % are based on mass unless otherwise specified.

EXAMPLE

<Evaluation of Physical Properties on Synthesis Talc>

With respect to synthetic talc prepared in Production example 1, synthetic talc prepared in Comparative production example 1 and commercial natural talc, physical properties were evaluated in accordance with the following methods, (Shape of Particle)

A mean long diameter and a mean short diameter of a particle were respectively determined by measuring a long diameter and a short diameter of ten particles, which were selected at random from particles having a long diameter and a short diameter capable of being measured by a scanning electron microscope (SEM) image and averaging the respective data. A mean thickness of a particle was determined by measuring a thickness of ten particles, which were selected at random from particles having a thickness capable of being measured by a SEM image and averaging the data. An aspect ratio was calculated by dividing the mean long diameter by the mean thickness.

(Elemental Analysis)

Mg and Si in a talc component were quantified using a plasma emission spectrometry analyzer (ICP-OES: IRIS Advantage by JAPAN Jarrell-Ash Company), and each value of x and y in the aforementioned formula (1) was calculated.

(Particle Size Distribution)

A particle size distribution was measured using a laser diffraction particle size distribution analyzer (LA-950 by Horiba Ltd.), and a mean volume particle size and a variation coefficient of particle size distribution was determined.

(BET Specific Surface Area)

BET specific surface area was measured using a specific surface area analyzer (AUTOSORB-1 by Quantachrome Instruments) in accordance with BET method.

(Powder X-Ray Diffraction Measurement: XRD)

Using a powder X-ray diffractometer (Ultima IV by Rigaku Corporation) and CuKα ray having a wavelength of 1.5406 Å, a powder X-ray diffraction (XRD) of unoriented particle was measured under following conditions.

Tube voltage and current value; 40 kV and 30 mA
Scanning speed; 2°
Sampling width; 0.02°
Divergence slit; ½°
Vertical divergence slit; 10 mm
Scattering slit; ½°
Light receiving slit; 0.3 mm A peak intensity and a half width at half maximum were determined based on XRD spectrum obtained.

(Thermogravimetric Analysis: TG)

Using a thermogravimeter (Thermoplus TG8120 by Rigaku Corporation), thermogravimetric analysis of particles was conducted in a range of from room temperature to 1,000° C. with a temperature elevation rate of 20° C./minute under an air atmosphere.

(Mean Dynamic Friction Coefficient Test)

A mean friction coefficient (MIU) and a fluctuation of mean friction coefficient (MMD) were measured using a friction tester available from Kato Tech Co., Ltd. Test samples were prepared by applying a powder for evaluation to an artificial leather (SAPURARE, Idemitsu Technofine Company) in an amount of 0.5 mg/cm$^2$. Meanwhile, the same artificial leather as that used for preparing the test sample was attached to a surface of a contact point in a sensor section, which touches a sample section, of the friction tester. Measurement was conducted under conditions that a load is 25 g, a sample movement speed is 1 mm/sec, and a range of measurement distance is 20 mm.

<Preparation of Talc for Evaluation>

Production Example 1

In an automatic mortar, 25 parts of silica gel (special grade reagent available from Kojundo Chemical Laboratory Co., Ltd.) was mixed with 25 parts of magnesium hydroxide (special grade reagent available from Kojundo Chemical Laboratory Co., Ltd.) for 1 hour. Subsequently, the resultant powdery mixture was filled into a gold tube. Next, 50 parts of purified water was poured into the gold tube, and then the mouth of the tube was sealed. This gold tube was set in a test tube type hydrothermal synthesis apparatus, and then hydrothermal synthesis was conducted without stirring at 600° C. for 5 days under a high pressure of 1,000 bar. The resultant powdery particle is referred to as synthetic talc A (Sample name).

Production Example 2

A powdery particle was obtained in the same manner as Production example 1 except that amounts of the silica gel and the magnesium hydroxide were varied to 28 parts and 22 parts, respectively. The powdery particle was referred to as synthetic talc B (Sample name).

Production Example 3

A powdery particle was obtained in the same manner as Production example 1 except that a temperature of the hydrothermal synthesis was varied to 500° C. from 600° C. The powdery particle was referred to as synthetic talc C (Sample name).

Comparative Production Example 1

A powdery particle was obtained in the same manner as Production example 1 except that a temperature and a reaction time of the hydrothermal synthesis were respectively varied to 300° C. from 600° C. and 7 days from 5 days. The powdery particle was referred to as synthetic talc D (Sample name).

Natural Talc 1 for Comparison

As a natural talc for comparison, a commercial dry-ground natural talc (SW-A available from Asada Milling Co., Ltd.) was prepared. The natural talc is referred to as natural talc A (Sample name).

Natural Talc 2 for Comparison

As another natural talc, a commercial wet-ground natural talc (SEX-15 available from Yamaguchi Mica Co., Ltd.) was prepared. The natural talc is referred to as natural talc B (Sample name).

<Evaluation Result of Synthetic Talc>

With respect to each of synthetic talcs prepared in production or comparative production examples and natural talc for comparison, physical properties were measured. Results are shown in Table 1.

Comparison of the data shown in Table 1 in connection with synthetic talcs A to C in production example 1 to 3, synthetic talc D in comparative production example 1, natural talc A and natural talc B indicates the followings.

(1) Each of synthetic talcs A to C is a powder having a narrow particle size distribution as seen from a small variation coefficient of particle size distribution in the measurement of mean volume diameter.

(2) Each of synthetic talcs A to C has a smaller thickness and a larger aspect ratio as compared with the natural talcs, and is a flat and slippery material.

(3) Each of synthetic talcs A to C is superior in a mean friction coefficient and a fluctuation of mean friction coefficient as compared with the natural talcs.

(4) Each of synthetic talcs A to C has a half width at half maximum of peak existing at 2θ equal to 9.4°±1° in unoriented powder X-ray diffraction measurement (XRD) which is close to that of natural talcs.

(5) Synthetic talc A containing more amount of Mg is superior to synthetic talc B, which is different only in a ratio of Mg/Si, in a mean friction coefficient and a fluctuation of mean friction coefficient.

Example 1 and Comparative Example 1 Face Powder

Face powders having the formulation shown in Table 2 were prepared according to the following production method, and were evaluated relative to spreadability on skin, skin compatibility, smoothness and fineness upon finishing, and transparent feel upon finishing. Results are shown in Table 2.

<Production Method>

I: Components 1 to 10 shown in Table 2 are mixed.

II: Components 11 to 14 are added to the mixture obtained in the above step I and then mixed.

TABLE 1

|  | Synthetic talc A | Synthetic talc B | Synthetic talc C | Synthetic talc D | Natural talc A | Natural talc B |
|---|---|---|---|---|---|---|
| x (number of Mg atom) | 3.73 | 3.11 | 3.73 | 3.73 | Unmeasured | Unmeasured |
| y (number of Si atom) | 3.59 | 3.95 | 3.59 | 3.59 | Unmeasured | Unmeasured |
| x/y | 1.04 | 0.79 | 1.04 | 1.04 | — | — |
| x + y | 7.32 | 7.06 | 7.32 | 7.32 | — | — |
| Mean long diameter (μm) | 0.67 | 0.67 | 0.65 | Unmesurable *1 | 11 | 18.6 |
| Mean short diameter (μm) | 0.41 | 0.42 | 0.38 | Unmesurable *1 | 4 | 5 |
| Thickness (μm) | 0.025 | 0.025 | 0.021 | Unmesurable *1 | 2 | 1.4 |
| Aspect ratio | 26.8 | 26.8 | 31.0 | — | 5.5 | 13.3 |
| volume mean particle diameter (μm) | 2.17 | 1.97 | 2.63 | Unmesurable *1 | 10.7 | 12.9 |
| variation coefficient of particle size distribution (%) | 13.3 | 20.8 | 25.5 | — | 111 | 31.3 |
| BET specific surface area (m²/g) | 17 | 15 | 20 | 306 | 4 | 5 |
| Mean friction coefficient (MIU) | 0.24 | 0.30 | 0.35 | 0.55 | 0.42 | 0.41 |
| Fluctuation of mean friction coefficient (MMD) | 0.0015 | 0.0018 | 0.003 | 0.004 | 0.0036 | 0.0032 |
| Half width at half maximum of peak existing at 2θ = 9.4° ± 1° | 0.10 | 0.13 | 0.15 | 0.81 | 0.10 | 0.05 |
| Ratio of peak intensity (9.4°/60.5°) | 4.5 | 4.6 | 2.6 | 1.0 | 12.2 | 125 |
| TG −2% ruduction temperature (° C.) | 828 | 867 | 869 | 58 | 879 | 947 |
| TG −5% ruduction temperature (° C.) | 909 | 901 | >1000 | 388 | 951 | >1000 |

*1 Unmesurable due to aggregation of fine particles.

<Evaluation Method>

Each of the face powders was evaluated by 10 female panelists in accordance with the organoleptic examination. Results of each evaluation items were shown in the following three levels.

Good: Evaluation point 2

Medium: Evaluation point 1

Poor: Evaluation point 0

Properties of the face powders were evaluated based on the following criteria.

| Judgement | Average evaluation point |
|---|---|
| 5 | 1.5 or more |
| 4 | 1.2 or more to less than 1.5 |
| 3 | 0.8 or more to less than 1.2 |
| 2 | 0.3 or more to less than 0.8 |
| 1 | less than 0.34 |

TABLE 2

Formulation (Parts by mass)

| | Component | Example 1 | Comparative example 1 |
|---|---|---|---|
| 1 | Synthetic talc prepared in Production example 1 | 10 | — |
| 2 | Comparative natural talc A | — | 10 |
| 3 | Mica | 25 | 25 |
| 4 | Titanium dioxide fine particle | 1 | 1 |
| 5 | Spherical silica | 4 | 4 |
| 6 | Spherical silicone powder (Note 1) | 1 | 1 |
| 7 | Red ocher coated with silicone | 0.3 | 0.3 |
| 8 | Zink iron oxide coated with silicone | 0.8 | 0.8 |
| 9 | Iron black coated with silicone | 0.1 | 0.1 |
| 10 | Sericite | 53.3 | 53.3 |
| 11 | Petrolatum | 1 | 1 |
| 12 | Squalane | 2 | 2 |
| 13 | Sorbitan sesquiisostearate | 0.5 | 0.5 |
| 14 | Ethylhexyl methoxycinnamate | 1 | 1 |
| | Total | 100 | 100 |
| | Result of evaluation | | |
| | Spreadability | 5 | 3 |
| | Skin compatibility | 5 | 3 |
| | Smoothness and fineness upon finishing | 5 | 3 |
| | Transparent appearance upon finishing | 5 | 4 |

(Note 1):
Tospearl 145 (Momentive Corp.)

As seen from the data shown in table 2, the face powder in example 1 of the invention was excellent in spreadability on skin, skin compatibility, and smoothness and fineness upon finishing. Also, it was excellent in transparent appearance upon finishing. To the contrary, the face powder using the conventional natural talc in comparative example 1 was insufficient in every evaluation items.

Example 2 Powder Foundation

A powder foundation was prepared in accordance with the following formulation and production method. The resultant powder foundation was excellent in spreadability on skin, skin compatibility, smoothness and fineness upon finishing, and transparent appearance upon finishing.

<Formulation>

| (Component) | (%) |
|---|---|
| 1. Synthetic talc B prepared in Production example 2 | 15 |
| 2. Synthetic mica (Note 2) | 10 |
| 3. Sericite | Balance |
| 4. Red ocher | 0.7 |
| 5. Yellow iron oxide | 1.5 |
| 6. Iron black | 0.3 |
| 7. Spherical silicone powder (note 1) | 5 |
| 8. Spherical urethane powder (note 3) | 5 |
| 9. Dimethylpolysiloxane (10CS) | 3 |
| 10. Liquid paraffin | 3 |
| 11. Petrolatum | 5 |
| 12. Sorbitan sesquiisostearate | 1 |
| 13. Antiseptic | proper quantity |
| 14. Antioxidant | proper quantity |

(note 2):
PDM-9WA (Topy Industries, Ltd.)
(note 3):
DAIMICBEAZ UCN-8070 CM CLEAR (Dainichiseika Colour & Chemicals Mfg. Co., Ltd.)

<Production Method>

I: Components 1 to 8 are mixed.

II: Components 9 to 14 are added to the mixture obtained in the above step I and then mixed.

III. The mixture obtained in the aforementioned step II is filled into a pan and compressed to make a powder foundation.

Example 3 O/W Type Emulsified Cream Foundation

An O/W type emulsified cream foundation was prepared in accordance with the following formulation and production method. The resultant O/W type emulsified cream foundation was excellent in spreadability on skin, skin compatibility, smoothness and fineness upon finishing, and transparent appearance upon finishing.

<Formulation>

| (Component) | (%) |
|---|---|
| 1. Synthetic talc A prepared in Production example 1 | 8.0 |
| 2. Sericite | 7.0 |
| 3. Mica | 6.0 |
| 4. Nylon powder | 3.0 |
| 5. Titanium dioxide | 3.0 |
| 6. Red ocher | 0.3 |
| 7. Yellow iron oxide | 0.7 |
| 8. Iron black | 0.1 |
| 9. Squalane | 10.0 |
| 10. Olive oil | 10.0 |
| 11. Ethylhexyl palmitate | 3.0 |
| 12. Stearic acid | 2.0 |
| 13. Glyceryl monostearate | 2.0 |
| 14. POE(40) sorbitan monostearate | 2.0 |
| 15. Glycerin | 5.0 |
| 16. 1,3-Butylene glycol | 5.0 |
| 17. Triethanol amine | 0.5 |
| 18. Antiseptic | proper quantity |
| 19. Antioxidant | proper quantity |

<Production Method>

I: Components 1 to 14 are melted by heating and mixed.

II: Components 15 to 19 are melted by heating and mixed.

III: The mixture obtained in step II is added to the mixture obtained in step I, and then the resultant mixture is emulsified. Subsequently, the resultant emulsion is cooled while agitating to prepare an emulsified foundation.

Example 4 W/O Type Sunscreen Milky Lotion

An O/W type sunscreen milky lotion was prepared in accordance with the following formulation and production method. The resultant O/W type sunscreen milky lotion was excellent in spreadability on skin and skin compatibility.

<Formulation>

| (Component) | (%) |
|---|---|
| 1. Synthetic talc A prepared in Production example 1 | 3.0 |
| 2. Titanium dioxide fine particle coated with silicone | 4.0 |
| 3. Zinc oxide fine particle coated with silicone | 8.0 |
| 4. Nylon powder | 3.0 |
| 5. Ethylhexyl methoxycinnamate | 5.0 |
| 6. Decamethyl cyclopentasiloxane | 30.0 |
| 7. PEG-10 dimethicone | 3.0 |
| 8. Ethylhexyl pulmitate | 3.0 |
| 9. Pentylene glycol | 2.0 |
| 10. 1,3-Butylene glycol | 4.0 |
| 11. Phenoxyethanol | 0.5 |
| 12. Purified water | Balance |

<Production Method>
I: Components 1 to 8 are mixed.
II: Components 9 to 12 are mixed.
III: The mixture obtained in step II is added to the mixture obtained in step I, and then the resultant mixture is emulsified to prepare a sunscreen milky lotion.

INDUSTRIAL APPLICABILITY

The cosmetic of the present invention is excellent in spreadability on skin, smoothness, skin compatibility, transparent appearance upon finishing and safety. Hence, it is suitable for a powder cosmetic and is also useful for a milky lotion type cosmetic such as emulsified foundation, milky lotion makeup base and sunscreen milky lotion. Further, it is useful for a cosmetic containing a synthetic talc as a main component such as baby powder.

What is claimed is:

1. A cosmetic comprising a synthetic talc, wherein the synthetic talc is a flake-like particle that has a basic structure in which an octahedron sheet is sandwiched between two tetrahedron sheets and contains a 2:1 type layered crystal of silicate represented by formula (1);

$$Mg_xSi_yO_{10}(OH)_2 \qquad (1)$$

in the formula (1), x and y are values satisfying conditions of 0.50≤x/y≤1.20 and 6.5≤x+y≤7.5, wherein the flake-like particle has a mean volume particle diameter of 0.5 to 100 μm, 0.3° or less of half width at half maximum of peak existing at 2θ equal to 9.4°±1° when measured by unoriented powder X-ray diffractometry (XRD) using CuKα ray, a BET specific surface area of 2 to 25 m²/g, and is substantially free of $Mg_3Si_2O_5(OH)$.

2. The cosmetic according to claim 1, wherein the flake-like particle has a variation coefficient of particle size distribution of 30% or less.

3. The cosmetic according to claim 1, wherein an intensity of peak existing at 2θ equal to 9.4°±1° when measured by unoriented powder X-ray diffractometry (XRD) is 2.5 times or more as compared to an intensity of peak existing at 2θ equal to 60.5°±1°.

4. The cosmetic according to claim 1, wherein the flake-like particle has 0.3 to 0.8 of a ratio of a mean short diameter to a mean long diameter in its crystal plane (a, b) (mean short diameter/mean long diameter), 0.01 to 1 μm of a mean thickness in its c-axis direction, and 10 to 500 of a mean aspect ratio (mean long diameter/mean thickness).

5. The cosmetic according to claim 1, wherein the flake-like particle has 0.40 or less of a mean friction coefficient (MIU) and 0.0035 or less of a fluctuation of mean friction coefficient (MMD).

6. The cosmetic according to claim 1, wherein the flake-like particle is a non-crushed particle which is obtained by hydrothermal synthesis.

7. The cosmetic according to claim 1, wherein the flake-like particle is obtained by a process comprising a step for preparing a raw material containing a magnesium hydroxide powder and a silica powder, and a step for conducting hydrothermal synthesis by heating the raw material at 500 to 800° C. under a pressure of 200 to 5,000 bar.

8. The cosmetic according to claim 1, wherein the cosmetic is a powdered cosmetic.

9. The cosmetic according to claim 1, wherein the cosmetic is in the form of liquid, milky lotion or cream.

10. The cosmetic according to claim 1, wherein the half width at half maximum of peak existing at 2θ equal to 9.4°±1° is 0.2° or less.

11. The cosmetic according to claim 1, wherein the ratio of Mg to Si is 0.80 to 1.2.

12. The cosmetic according to claim 2, wherein the flake-like particle has 0.3 to 0.8 of a ratio of a mean short diameter to a mean long diameter in its crystal plane (a, b) (mean short diameter/mean long diameter), 0.01 to 1 μm of a mean thickness in its c-axis direction, 10 to 500 of a mean aspect ratio (mean long diameter/mean thickness), 0.40 or less of a mean friction coefficient (MIU) and 0.0035 or less of a fluctuation of mean friction coefficient (MMD).

13. The cosmetic according to claim 12, wherein an intensity of peak existing at 2θ equal to 9.4°±1° when measured by unoriented powder X-ray diffractometry (XRD) is 2.5 times or more as compared to an intensity of peak existing at 2θ equal to 60.5°±1°.

14. The cosmetic according to claim 12, wherein the mean thickness in its c-axis direction is 0.02 to 0.3 μm and the mean aspect ratio is 15 to 300.

15. The cosmetic according to claim 4, wherein the mean long diameter in its crystal plane (a, b) is 0.5 to 30 μm.

* * * * *